US009060747B2

(12) United States Patent
Salorio

(10) Patent No.: US 9,060,747 B2
(45) Date of Patent: Jun. 23, 2015

(54) DEVICE TO MONITOR AND TREAT HEMIPLEGIA AND HEMISPATIAL NEGLECT

(75) Inventor: Cynthia Salorio, Baltimore, MD (US)

(73) Assignees: The Johns Hopkins University, Baltimore, MD (US); Kennedy Krieger Institute, Inc., Baltimore, MD (US)

( * ) Notice: Subject to any disclaimer, the term of this patent is extended or adjusted under 35 U.S.C. 154(b) by 153 days.

(21) Appl. No.: 13/641,562

(22) PCT Filed: Apr. 12, 2011

(86) PCT No.: PCT/US2011/032024
§ 371 (c)(1),
(2), (4) Date: Jan. 15, 2013

(87) PCT Pub. No.: WO2011/130202
PCT Pub. Date: Oct. 20, 2011

(65) Prior Publication Data
US 2013/0110009 A1  May 2, 2013

Related U.S. Application Data

(60) Provisional application No. 61/324,852, filed on Apr. 16, 2010.

(51) Int. Cl.
*A61B 5/117*  (2006.01)
*A61B 5/103*  (2006.01)
*A61B 5/00*  (2006.01)
(Continued)

(52) U.S. Cl.
CPC .................. *A61B 5/74* (2013.01); *A61M 21/00* (2013.01); *A61M 2021/0022* (2013.01);
(Continued)

(58) Field of Classification Search
USPC ................... 600/301, 557, 587, 595; 463/37; 33/512; 455/404.1, 404.2, 456.1
See application file for complete search history.

(56) References Cited

U.S. PATENT DOCUMENTS 5,562,707 A   10/1996  Prochazka et al.
5,861,797 A    1/1999  Becker
(Continued)

FOREIGN PATENT DOCUMENTS

JP   2006-006916 A   1/2006
JP   2009-112791 A   5/2009
(Continued)

*Primary Examiner* — Brian Szmal
(74) *Attorney, Agent, or Firm* — Johns Hopkins Technology Transfer

(57) ABSTRACT

A programmable device adaptable for wearing on an affected limb of a subject afflicted with hemiplegia and/or hemispatial neglect includes a sensor for measuring movement values of the affected limb, a sensory stimulator for providing sensory stimulation at a particular interval, duration, frequency, intensity and/or pattern, a microprocessor for storing and administering the one or more interval values and the one or more duration values of the sensory stimulation, and a computer interface for transferring and receiving data between the microprocessor and a separate data processor. The programmable device provides cues to a subject according to preset parameters or when it has been determined that the affected limb is not being used. A method for monitoring and treating a subject afflicted with hemiplegia and/or hemispatial neglect is also disclosed.

24 Claims, 2 Drawing Sheets

(51) Int. Cl.
  *A61M 21/00* (2006.01)
  *G06F 19/00* (2011.01)
  *A61B 5/11* (2006.01)
(52) U.S. Cl.
  CPC ............. *A61M 2021/0027* (2013.01); *A61M 2021/0044* (2013.01); *A61M 2021/0072* (2013.01); *A61M 2209/088* (2013.01); *G06F 19/3481* (2013.01); *A61B 5/1118* (2013.01); *A61B 5/7405* (2013.01); *A61B 5/742* (2013.01); *A61B 5/7455* (2013.01); *G06F 19/00* (2013.01)

(56) References Cited

U.S. PATENT DOCUMENTS 8,273,036 B2 * 9/2012 Fong .................... 600/595
2011/0040204 A1 * 2/2011 Ivorra et al. .............. 600/557

FOREIGN PATENT DOCUMENTS

WO  2006-021952 A2  3/2006
WO  2007-047852 A2  4/2007

* cited by examiner

DEVICE TO MONITOR AND TREAT HEMIPLEGIA AND HEMISPATIAL NEGLECT

CROSS-REFERENCE TO RELATED APPLICATIONS

This application is a 35 U.S.C. §371 U.S. national entry of International Application PCT/US2011/032024 having an international filing date of Apr. 12, 2011, which claims the benefit of U.S. Provisional Application No. 61/324,852, filed Apr. 16, 2010, the content of each of the aforementioned applications is herein incorporated by reference in their entirety.

FIELD OF THE INVENTION

The present invention pertains to a method and programmable device for monitoring and treating hemiplegia and/or hemispatial neglect. More particularly, the present invention pertains to a method and programmable device which is incorporated into a wristband for monitoring and treating hemiplegia and/or hemispatial neglect.

BACKGROUND OF THE INVENTION

Hemiplegia is a paralysis on one side of the body, contralateral to the affected hemisphere of the brain. Hemiplegia may be caused by stroke, infection, traumatic brain injury, or the like, or may exist at birth, such as in individuals with cerebral palsy. With intensive intervention, lower extremity functioning typically recovers enough for the affected individuals to walk (albeit with gait disturbances); however, upper extremity dysfunction (i.e., hand and arm use) is generally persistent regardless of intervention.

Hemispatial neglect is a neuropsychological condition defined as an inattention to the side of space opposite the affected hemisphere. Hemispatial neglect typically affects all senses, including vision, hearing, and touch. Long-term functional recovery is poor and negatively impacts quality of life.

Children and adults with intractable epilepsy, brain surgery, stroke, or other acquired brain injury often have hemispatial neglect. Hemispatial neglect affects all senses in that such individuals do not notice items on that side, are less likely to respond to sound on that side, and, importantly, "forget" to use their arm on that side. The arm on that side tends to be weaker because of the underlying brain condition. The neglect exacerbates this weakness because the arm is rarely used. Often the individuals are physically able to use the arm far more than they actually do.

It has been discovered that if an affected individual is reminded to use the arm, or look to the affected side, either verbally or with a tap on the arm or table, they can often do so. To address this issue, the inventor of the present application has examined use of a vibrating alarm watch which is placed on the affected individual's "forgotten" side. The intermittent vibration will cue the individual to the affected arm and also will send a signal to the part of the brain that is controlling the arm, thereby hopefully strengthening the connection. Especially with young children, however, commercially available vibrating watches are bulky and have a limited ability to set specified operating parameters. Additionally, commercially available watches do not have the capability to measure arm use or provide data on whether the device is effective in increasing movement of the arm.

Accordingly, there is a need in the art for a device and method for monitoring and treating a subject afflicted with hemiplegia and/or spatial neglect that is not bulky, and also provides additional capabilities for monitoring, the feedback as to whether the device is effective in increasing movement of the arm.

SUMMARY

According to a first aspect of the present invention, a programmable device adaptable for wearing on an affected limb of a subject afflicted with hemiplegia, hemispatial neglect, or both, comprises a sensor for measuring movement values of the affected limb, a sensory stimulator for providing sensory stimulation at one or more interval values and one or more duration values, as microprocessor for storing and administering the one or more interval values and the one or more duration values of the sensory stimulation, and a computer interface for transferring and receiving data between the microprocessor and a separate data processor.

According to a second aspect of the present invention, a method for monitoring and treating a subject afflicted with hemiplegia, hemispatial neglect, or both, comprises positioning, a programmable device on an affected limb of the subject, the programmable device including a sensory stimulator for providing sensory stimulation and a sensor for measuring movement of the affected limb measuring movement values of the affected limb transferring the measured movement values to a separate data processor, determining one or more sensory stimulation interval values and one or more sensory stimulation duration values, and transferring the one or more sensory stimulation interval values and the one or more sensory stimulation duration values to the programmable device.

According to a third aspect of the invention, a method for monitoring and treating as subject afflicted with hemiplegia, hemispatial neglect, or both, comprises receiving measured values of a sensor related to movement of the affected limb of a subject from a programmable device, comparing the measured values of movement to a set of reference values using a computer algorithm, and determining one or more sensory stimulation interval values and one or more sensory stimulation duration values based on the comparing the set of reference values to the measured movement values using said computer algorithm.

According to a fourth aspect of the invention, a computer-readable medium comprises software, wherein, when executed by a computer, causes the computer to receive measured movement values from at sensor related to movement of an affected limb of a subject, compare the measured movement values to a set of reference values using a computer algorithm, and determine one or more sensory stimulation interval values and one or more sensory stimulation duration values based on said comparing said set of reference values to said measured movement values using said computer algorithm.

BRIEF DESCRIPTION OF THE DRAWINGS

The accompanying drawings provide visual representations which will be used to more fully describe the representative embodiments disclosed herein and can be used by those skilled in the art to better understand them and their inherent advantages. In these drawings, like reference numerals identify corresponding elements and.

DETAILED DESCRIPTION OF THE PREFERRED EMBODIMENTS

Figure 1:
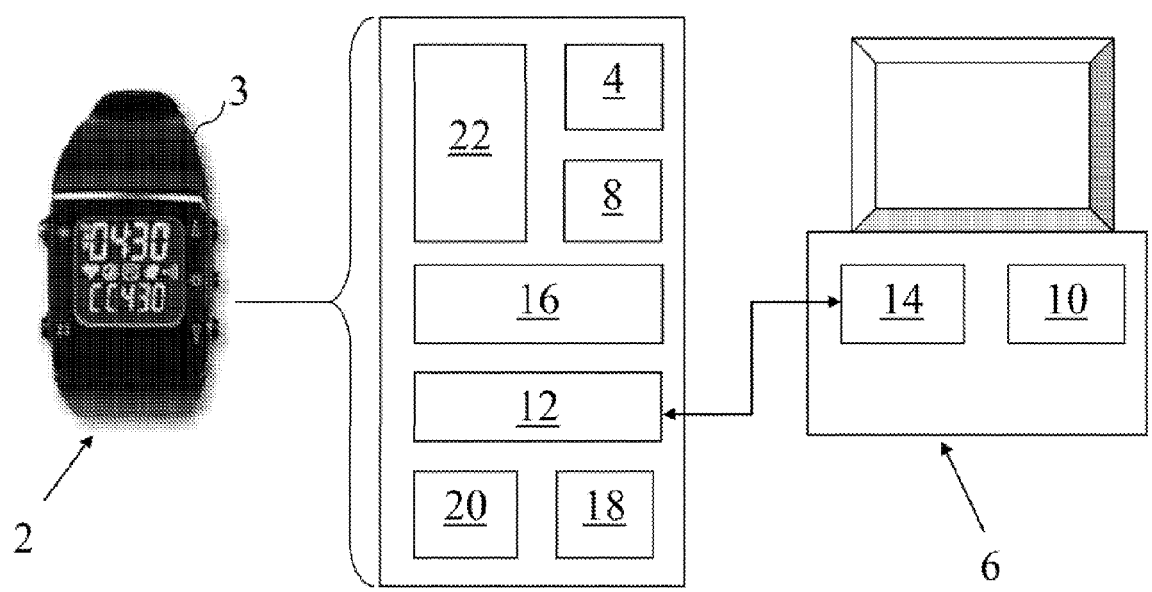
FIG. 1 is a schematic of the vibrating band and its accompanying features and interface with a data processor.

The presently disclosed subject matter ma be embodied in many different forms and should not be construed as limited to the embodiments set forth herein; rather, these embodiments are provided so that this disclosure will satisfy applicable legal requirements. Indeed, many modifications and other embodiments of the presently disclosed subject matter set forth herein will come to mind to one skilled in the art to which the presently disclosed subject matter pertains having the benefit of the teachings presented in the foregoing descriptions and the associated Drawings. Therefore, it is to be understood that the presently disclosed subject matter is not to be limited to the specific embodiments disclosed and that modifications and other embodiments are intended to be included within the scope of the appended claims.

Although specific terms are employed herein, they are used in a generic and descriptive sense only and not for purposes of limitation. Unless otherwise defined, all technical and scientific terms used herein have the same meaning as commonly understood by one of ordinary skill in the art to which this presently described subject matter belongs.

Following long-standing patent law convention, the terms "a," "an" and "the" refer to "one or more" when used in this application, including the claims. Thus for example, reference to "a subject" includes a plurality of subjects, unless the context clearly is to the contrary (e.g., a plurality of subjects), and so forth.

Throughout this specification and the claims, the terms "comprise." "comprises," and "comprising" are used in a non-exclusive sense, except where the context requires otherwise. Likewise, the term "include" and its grammatical variants are intended to be non-limiting, such that recitation of items in a list is not to the exclusion of other like items that can be substituted or added to the listed items.

For the purposes of this specification and appended claims, unless otherwise indicated, all numbers expressing amounts, sizes, dimensions, proportions, shapes, formulations, parameters, percentages, parameters, quantities, characteristics, and other numerical values used in the specification and claims, are to be understood as being modified in all instances by the term "about" even though the term "about" may not expressly appear with the value, amount or range. Accordingly, unless indicated to the contrary, the numerical parameters set forth in the following specification and attached claims are not and need not be exact, but may be approximate and/or larger or smaller as desired, reflecting tolerances, conversion factors, rounding off, measurement error and the like, and other factors known to those of skill in the art depending on the desired properties sought to be obtained by the presently disclosed subject matter. For example, the term "about," when referring to as value can be meant to encompass variations of, in some embodiments, ±100% in some embodiments 50%, in some embodiments ±20%, in some embodiments ±10%, in some embodiments ±5%, in some embodiments ±1%, in some embodiments ±0.5%, and in some embodiments ±0.1% from the specified amount, as such variations are appropriate to perform the disclosed methods or employ the disclosed compositions.

Further, the tom "about" when used in connection with one or more numbers or numerical ranges, should be understood to refer to all such numbers, including all numbers in a range and modifies that range by extending the boundaries above and below the numerical values set forth. The recitation of numerical ranges by endpoints includes all numbers, e.g., whole integers, including fractions thereof, subsumed within that range for example, the recitation of 1 to 5 includes 1, 2, 3, 4, and 5, as well as fractions thereof, e.g., 1.5, 2.25, 3.75, 4.1, and the like) and any range within that range.

In some embodiments, the presently disclosed subject matter provides a tool for monitoring and treating hemiplegia and/or hemispatial neglect after hemispherectomy surgery in patients, including children. Hemiplegia and hemispatial neglect, however, is a much broader problem in both children and adults with a variety of neurological conditions, including acquired brain injury (e.g., traumatic brain injury (TBI), stroke, brain tumors, brain surgery, encephalitis, and the like), and neurodevelopmental conditions (e.g., cerebral palsy). Thus, the presently disclosed device and methods can be used as a tool to monitor and treat hemispatial neglect across age groups and etiologies. However, it should be understood that the method and device of the present invention may also be used to monitor and treat animals, and the like.

More particularly, the presently disclosed subject matter provides a programmable device to provide sensory stimulation and a "reminder" to patients afflicted with hemiplegia and or hemispatial neglect to use the affected arm. The sensory stimulation also will draw attention to the neglected side of space and also will send a sensory signal to the area of the brain subserving the sensory detection for the limb. The presently disclosed programmable device in its several embodiments includes features to enhance its ease of use and enhance its ultimate therapeutic effect. Such features include, but are not limited to waterproofing, different color choices, ability to have varying intervals between stimulations, varying intensities of stimulation (such as vibratory, auditory, or visual stimulation), varying duration of stimulation, varying patterns of vibration, and the ability to have the stimulation activate only when the patient is not using the affected arm for a set period of time.

With reference to FIG. 1, an exemplary programmable device 2 adaptable for wearing on an affected limb of as subject afflicted with hemiplegia and/or hemispatial neglect is illustrated. The device 2 preferably includes a band 3 for securing the programmable device 2 on an affected limb of the subject. The programmable device 2 may be positioned on the band 3, or within the hand 3, depending on application and design preference. In this way, the band may he hollowed to allow for the components of the device. Alternatively, the programmable device 2 may be secured or incorporated onto a band, similar to how a watch face is incorporated onto a wrist band. The band 3 preferably has adjustable straps that allow it to be secured in various sizes of limbs. In this way, the band 3 may have complimentary Velcro straps, to easily adapt the size of the limb of the subject. In addition, the band 3 may be made of elastic for easy securing to a user, or may be similar to a watch band, or the like, although any type of material strap material is possible. Moreover, it should be understood that a band 3 is not necessary, and that the programmable device 2 may be affixed to any article or device that allows it be secured around the affected limb of the subject. Preferably, the programmable device is secured around the wrist of the patient but may be disposed at any location on the arm and/or leg. However, the wrist is the optimal location, because of the numerous nerve endings, etc.

As described above, the device 2 is designed to sense movement (or lack thereof) of an affected limb of a subject, which provides useful information as to whether the affected limb is being properly used, and to investigate the efficacy of various therapeutic interventions and/or therapy outcomes. Accordingly, a sensor 4 is provided for measuring and storing movement of the programmable device 2, which is subsequently transmitted to a separate data processor or computer 6 for data storage and analysis, as will be described in more detail below.

Preferably, the sensor 4 is a three-axis accelerometer, which measures and records movement values (i,e., trajectory, force and speed) of the affected limb. The sensor 4 may also include a gyroscope for measuring and recording the position of the affected limb. However, it should be understood that any type of sensor may be used for measuring movement of the affected limb, depending upon application and design preference.

The programmable device 2 also includes a sensory stimulator it to providing sensory stimulation at one or more interval values and one or more duration values. The sensory stimulation helps encourage the process of cortical reorganization by sending sensory information to the brain, and strengthening the connection between awareness and motor control of the affected limb. Preferably, the sensory stimulator 8 is a vibration device. In a more preferred embodiment, the vibration device is a shaftless pager motor. However, it should he understood that any type of vibration device be including, depending upon application and design preference. In addition, the sensory stimulator 8 may be an audible device for producing an audible stimulation, such as a buzzer or alarm, or a visual device for producing a visual stimulation, or any combination of sensory stimulators. For example, the programmable device 2 may include both a vibration device as well as an alarm, providing cues to the subject regarding non-use of the affected limb.

As described above, the sensory stimulator 8 provides stimulation at one or more interval values and one or more duration values. However, the sensory stimulator 8 may provide stimulation according to a prescribed pattern, intensity, and/or frequency. Preferably, these values are set by software 10 provided in the separate data processor 6, and then transferred through a computer interface 12 of the programmable device 2. The values may be set manually by the doctor or clinician, or automatically through software. When set manually, the device can be programmed by the clinician (or eventually, the parent or adult supervisor) at a specific time duration, interval, strength, frequency, and/or pattern.

In addition, the set of values may be set automatically through use of a computer algorithm contained in the software 10 of the separate data processor 6. In particular, the separate data processor 6 includes a computer-readable medium comprising the software 10, wherein, when executed by the data processor 6, causes the data processor 6 to (1) receive measured movement values kern a sensor related to movement of an affected arm of a subject. (2) compare the measured movement values to a set of reference values using a computer algorithm, and (3) determine one or more sensory stimulation interval values and one or more sensory stimulation duration values based on the comparing step (2). The set of reference values may be programmed within the software, but may also be manually inputted into the program by the clinician. When programmed with software, the set of values may be based upon particular measurements obtained from individuals unaffected by hemiplegia and/or hemispatial neglect. Alternatively, the set of values may be based upon previous reference values collected from the patients themselves. The algorithm can then determine what the appropriate treatment level would be.

As described above, the computer interface 12 transfers data related to the sensed movement to a computer interface 14 of the separate data processor 6. That is, the computer interface 12 of the programmable device 2 and the computer interface of the separate data processor 6 are in bi-directional communication. In this way, the separate data processor 6 can analyze the data through as software program to determine appropriate levels of stimulation to be provided, based upon the movement. Preferably, the data is transferred and received in real time wirelessly, through smart phone technology or wireless Wi-Fi technology. Alternatively, the data may be transferred and received via a USB cable, or the like. However, it should be understood that the data may be transferred to a particular website, that includes the software for processing data and providing the feedback to the programmable device 2. It should be understood that numerous networking configurations are possible, depending upon application and design preference, which are the scope of the invention.

Once the appropriate levels of stimulation are determined, the values acre transferred to the programmable device via computer interface 12. A microprocessor 16 can then store the transferred values and administer the values to the sensory stimulator 8. Accordingly, the microprocessor 16 is adapted to receive a command, such as one or more stimulation parameters, from the computer interface 12 of the programmable device 2. The sensory values can be stored in a memory device 18, such as an eeprom memory (non-volatile) memory, or the like.

The programmable device 2 also includes a cell battery for powering the device. The cell battery is preferably rechargeable, and may be charged by delivering battery charge current through a USB cable. The programmable device 2 may also include a programmable LCD screen 22. The LCD screen would allow for real-time control of the device 2, such as powering the device of and the like. However, the use of an LCD screen is optional, as the entire device may be programmed via the separate data processor 6.

Figure 2:
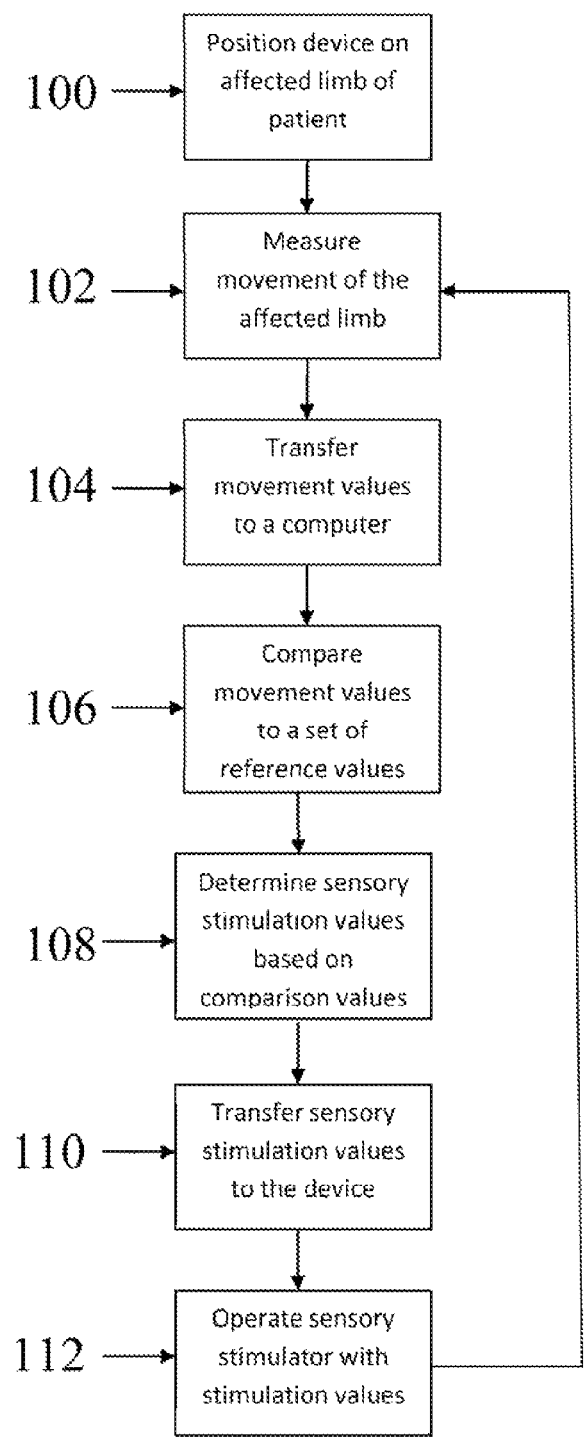
FIG. 2 is a flow diagram of the method for monitoring and treating a subject afflicted with hemiplegia and/or hemispatial neglect.

With reference to FIG. 2, a flow diagram of a method for monitoring and treating a subject afflicted with hemiplegia and/or hemispatial neglect is illustrated. At step 100, the device is positioned on the affected limb of a subject. Prior to step 100, the device may have been manually programmed by the clinician to provide stimulation at present values, or at no values. If no values are entered, the method is useful for accessing the optimal values for the particular subject. If preset values are entered for stimulation, then steps 106 and 108 may be omitted, as will be described in more detail below.

At step 102, the movement values are measured. These movement values are transferred to the separate data processor at step 104. The transferred movement values are then compared to a set of reference values at step 106. From this comparison, a set of sensory stimulation input values are determined (step 108). These values are then transferred to the device (110), where the sensory stimulator is operated according to the transferred sensory stimulation values (step 112). After the data is transferred to the device, the process begins again at step 102, wherein movement values are measured. As described above, if preset values for stimulation are used, then steps 106 and 108 may be omitted.

In representative embodiments, the computer interface is capable of controlling a power on and/or a power off of the wristband. In other embodiments, the microcontroller is capable of performing an interrupt and ultra low power wake up functionality. The microcontroller may also be capable of being set to a sleep mode through the computer interface and turning off the system when the battery reaches a low voltage. In addition, data may be sent from the programmable device 2 regarding limb movements when charging the device, preferably through a USB connection.

The programming capabilities also can include embodiments in which the device can be programmed to vibrate at fixed intervals, randomized intervals, or when there is no motion (as measured by the sensor) over a certain period of time. Software can be installed on the clinical investigator's laptop for data collection and to program the wristbands. As described above, the sensory stimulation may be operated at fixed interval vibration, wherein the wristband is programmed to vibrate at a fixed interval (e.g., every 10 minutes, 2-3 second vibration), random interval vibration, wherein the wristband is programmed to vibrate at random intervals ranging, for example, from 5 to 30 minutes, and controlling vibration, wherein the wristband is programmed with no vibration to act as a control condition.

Subjects can be instructed to wear the wristband during waking hours (i.e., put it on and turn on the device when you get dressed, take it off when you go to bed). In embodiments wherein the subject is a child, as parent or other supervising adult can help them remember to use the device and ensure appropriate usage. Parents or other supervising adults of children subjects can be instructed to download data daily when they charge the device. Parents will be prompted, for example, by e-mail to report their child's tolerance and compliance with wearing the device on a daily basis. Subjects can be asked to wear the device for a period of time, e.g., one week, at which time feedback regarding tolerability and clinical improvements can be elicited and used to further modify the device's specifications and/or methods of use.

In addition, the microprocessor 16 of the programmable device 2 can be programmed such that certain movement parameters of the affected limb as detected by the sensor 4 will lead to the transfer of data to a separate device that would sound an alarm. For example, if detected movement is consistent with a fall, getting out of bed, a seizure activity, or other traumatic event, the software 10 can send a signal to a separate device, which would sound an alarm to alert a caregiver, parent, health care professional, or the like, regarding the event.

Further, the system can be programmed on the computer interface by specifying vibration interval and vibration duration values or entering the values into the computer, and the computer can be capable of saving the vibration interval and vibration duration entered into the program. In other embodiments, the user can enter the vibration duration and vibration interval variables directly into the computer, e.g., through keystroke entries, as described above.

The presently disclosed device is non-invasive, simple, easy to use, does not require constant parent, caregiver or therapist monitoring, allows the user to program various intervals, intensities, patterns, frequencies, and durations, and collects information about actual function of the limb, wherein the information is easily downloadable through a simple computer interface. The presently disclosed device would provide consistent cues to individuals to attend to the affected arm and area of space, thus counteracting potential effects of neglect and learned non-use on recovery (or development) of functional motor skills.

The presently disclosed device can be used as a tool to monitor and treat hemispatial neglect following hemispherectomy surgery, acquired brain injury, or other neurological insults. This device, and methods of use thereof, can provide consistent cues to patients, including children, to attend to the affected arm and area of space, thus counteracting potential effects of neglect and learned non-use on recovery (or development) of functional motor skills. Further, sensory stimulation could help encourage the process of cortical reorganization and strengthen the connection between awareness and motor control of the limb.

In certain embodiments, the device and its use could be implemented immediately after hemispherectomy surgery while the subjects participate in conventional inpatient rehabilitation. Further, the presently disclosed device and methods can be included as an adjunct therapy in intervention and rehabilitation programs. The present invention may also be used in connection with neuroimaging and diffusion tensor imaging to examine the effects of therapeutic interventions on cortical remapping of motor functions of individuals affected with certain neurological disorders. Moreover, it should be understood that the programmable device and method of the present invention may be used in as number of different settings, including but not limited to a hospital setting (acute care, acute rehabilitation, chronic rehabilitation), a nursing home, at home, or in therapy sessions and at any stage after the injury or during rehabilitation, not just acutely thereafter.

Although the present invention has been described in connection with preferred embodiments thereof, it will be appreciated by those skilled in the art that additions, deletions, modifications, and substitutions not specifically described may be made without departing from the spirit and scope of the invention as defined in the appended claims.

What is claimed is:

1. A programmable device adaptable for wearing on an affected limb of a subject afflicted with hemiplegia, hemispatial neglect, or both, comprising:
   a housing wherein the housing is configured to be worn on the affected limb;
   a sensor for measuring movement values of the affected limb;
   a sensory stimulator for providing sensory stimulation at one or more interval values and one or more duration values, wherein the interval values and duration values are determined by a comparison of movement of the affected limb to a set of reference values;
   a microprocessor for storing and administering the one or more interval values and the one or more duration values of the sensory stimulation; and
   a computer interface for transferring and receiving data between the microprocessor and a separate data processor.

2. The programmable device of claim 1, wherein said computer interface is configured to transfer movement values from the device to the separate data processor, and receives the one or more interval values and one or more duration values from the separate data processor.

3. The programmable device of claim 1, wherein said sensory stimulator is configured to provide the sensory stimulation at one or more sensory stimulation pattern values, one or more sensory stimulation intensity values, and one or more sensory stimulation frequency values.

4. The programmable device of claim 1, wherein the data is transferred and received in real time wirelessly.

5. The programmable device of claim 1, wherein the data is transferred and received at a fixed time when said programmable device is connected to the separate data processor.

6. The programmable device of claim 1, further including a band for securing the programmable device on the affected limb of the subject.

7. The programmable device of claim 6, wherein the programmable device is contained within the band.

8. The programmable device of claim 1, wherein the sensory stimulator is a vibration device for producing a vibration.

9. The programmable device of claim 1, wherein the sensory stimulator is an audible device for producing an audible stimulation.

10. The programmable device of claim 1, wherein the sensory stimulator is a visual device for producing a visual stimulation.

11. The programmable device of claim 1, further including a cell battery for powering the device, the cell battery being rechargeable.

12. The programmable device of claim 1, wherein the sensor is a three-axis accelerometer for measuring and recording a trajectory, force and speed of the affected limb.

13. The programmable device of claim 12, wherein the sensor further includes a gyroscope for measuring and recording position of the affected limb.

14. A method for monitoring and treating a subject afflicted with hemiplegia, hemispatial neglect, or both, comprising:
   positioning a programmable device on an affected limb of the subject, said programmable device including a sensory stimulator for providing sensory stimulation and a sensor for measuring movement of the affected limb;
   securing the programmable device to an affected limb of the subject with a housing for the programmable device;
   measuring movement values of the affected limb;
   transferring the measured movement values to a separate data processor;
   determining one or more sensory stimulation interval values and one or more sensory stimulation duration values, wherein the interval values and duration values are determined by a comparison of the movement values of the affected limb to a set of reference values; and
   transferring the one or more sensory stimulation interval values and the one or more sensory stimulation duration values to the programmable device.

15. The method of claim 14, wherein the one or more sensory stimulation interval values and one or more sensory stimulation duration values are determined manually.

16. The method of claim 14, wherein the one or more sensory stimulation interval values and one or more sensory stimulation duration values are determined using a computer algorithm.

17. The method of claim 14, further comprising stimulating the affected limb with the sensory stimulator at the one or more sensory stimulation interval values and the one or more sensory stimulation duration values.

18. The method of claim 17, further comprising stimulating the affected limb with the sensory stimulator at the one or more sensory stimulation interval values and the one or more sensory stimulation duration values when said movement values of said sensor indicate non-use of the affected limb for a set period of time.

19. The method of claim 14, further comprising determining one or more sensory stimulation pattern values, one or more sensory stimulation intensity values, and one or more sensory stimulation frequency value.

20. A method for monitoring and treating a subject afflicted with hemiplegia and/or hemispatial neglect, comprising:
   receiving measured values of a sensor related to movement of an affected limb of a subject from a programmable device secured to the affected limb;
   comparing the measured values of movement to a set of reference values using a computer algorithm; and
   determining one or more sensory stimulation interval values and one or more sensory stimulation duration values based on said comparing said set of reference values to said measured movement values using said computer algorithm.

21. The method of claim 20, further comprising transferring the one or more sensory stimulation interval values and the one or more sensory stimulation duration values to the programmable device.

22. The method of claim 20, further comprising determining one or more sensory stimulation pattern values, one or more sensory stimulation intensity values, and one or more sensory stimulation frequency value based on said comparing said set of reference values to said measured movement values using said computer algorithm.

23. A non-transitory computer-readable medium comprising software, wherein, when executed by a computer, causes the computer to:
   receive measured movement values from a sensor related to movement of an affected limb of a subject;
   compare the measured movement values to a set of reference values using a computer algorithm; and
   determine one or more sensory stimulation interval values and one or more sensory stimulation duration values based on said comparing said set of reference values to said measured movement values using said computer algorithm.

24. The non-transitory computer-readable medium of claim 23, further comprising determining one or more sensory stimulation pattern values, one or more sensory stimulation intensity values, and one or more sensory stimulation frequency value based on said comparing said set of reference values to said measured movement values using said computer algorithm.

* * * * *